United States Patent [19]

Frontini et al.

[11] Patent Number: 5,206,006
[45] Date of Patent: Apr. 27, 1993

[54] STABILIZED TRINDER REAGENT

[75] Inventors: Dario Frontini, Milan; Maurizio D'Alterio, Brugherio, both of Italy

[73] Assignee: Instrumentation Laboratory SpA, Milan, Italy

[21] Appl. No.: 852,816

[22] Filed: Mar. 17, 1992

Related U.S. Application Data

[62] Division of Ser. No. 575,206, Aug. 30, 1990, Pat. No. 5,108,733.

[51] Int. Cl.$^5$ .................... G01N 33/15; C12Q 1/28
[52] U.S. Cl. ................................ 424/7.1; 435/28
[58] Field of Search ........................... 424/7.1; 435/28

[56] References Cited

U.S. PATENT DOCUMENTS

| Re. 29,498 | 12/1977 | Meiattini | 435/14 |
| 3,992,158 | 11/1976 | Przybylowicz | 422/57 |
| 4,716,110 | 12/1987 | Wada et al. | 435/25 |

FOREIGN PATENT DOCUMENTS

| 0071730 | 2/1983 | European Pat. Off. |
| 0123115 | 10/1984 | European Pat. Off. |
| 0230229 | 7/1987 | European Pat. Off. |
| 560828 | 9/1984 | Fed. Rep. of Germany |
| 8604610 | 8/1986 | PCT Int'l Appl. |

OTHER PUBLICATIONS

Putz et al., Am. Jour. Med. Technology vol. 42(10) 1976. pp. 351-356.
Ziebig et al., "Investigations of the Effect of Ascorbic Acid on Glucose Determination in the GOD-PAP Method", Zentralbl. Pharm. 125, (1986) pp. 223-227.

Primary Examiner—Allen J. Robinson
Assistant Examiner—Gary E. Hollinden
Attorney, Agent, or Firm—Testa, Hurwitz & Thibeault

[57] ABSTRACT

Spontaneous aspecific coloration in so-called Trinder reagents which can alter subsequent colorimetric determinations is inhibited by adding compounds of the chelating agent class to the solution. The resultant compositions contain a peroxidase enzyme, a phenylpyrazone derivative, a compound of phenolic or aromatic amine structure and a stabilizer. Preferred stablizers are ethylenediaminetetraacetic acid (EDTA) and diethylenetriaminepentaacetic acid (DTPA).

9 Claims, 8 Drawing Sheets

STABILIZED TRINDER REAGENT

This is a divisional of copending application Ser. No. 07/575,206 filed on Aug. 30, 1990, U.S. Pat. No. 5,108,733.

BACKGROUND OF THE INVENTION

The "Trinder reaction", named after its discoverer, is a reaction for detecting hydrogen peroxide evolved in a solution, by producing a colored compound. The colored compound which develops can then be determined spectrophotometrically.

Color development by hydrogen peroxide is obtained if a peroxidase enzyme, phenylpyrazone derivative and a compound of phenolic or aromatic amine structure are present in the solution. It should be noted that the expression "Trinder reaction" has a wider meaning herein than the reaction originally conceived by Trinder (A., Clin. Biochem., 6, 24, 1969) in which a peroxidase, 4-aminoantipyrine and phenol were used.

The Trinder reaction, when taken in its stated wider sense, is commonly used as an indicator reaction in clinical chemistry for determining numerous substrates, including uric acid, cholesterol, glucose, triglycerides etc. For example:

reagent uric acid: Uricase $\rightarrow H_2O_2 \rightarrow$ Trinder reagent cholesterol: Cholesterol Oxidase $\rightarrow H_2O_2 \rightarrow$ Trinder One of the biggest problems in the use of this reaction is the spontaneous aspecific coloration which occurs with time and which is accelerated by particular conditions such as storage at temperatures exceeding refrigerator temperatures or exposure to light.

This increase in coloration has been a serious obstacle in the use of Trinder reagents after a certain period of time because it reduces the photometric linearity range or the wavelength used in determining the coloration.

The availability of a preparation containing the Trinder reaction reagents with which the aforesaid drawbacks are absent is therefore of obvious importance.

SUMMARY OF THE INVENTION

The present invention therefore relates to a new method for inhibiting the spontaneous development of coloration in reagents for Trinder reactions, characterized by the use of chelating agents as stabilizers.

The present invention also relates to a composition of the Trinder type for detecting hydrogen peroxide evolved in a solution, comprising:
a) a phenylpyrazone derivative,
b) a phenol or an aromatic amine,
c) a peroxide enzyme,
d) aqueous buffer, and
e) a polyalkylaminepolyacetic acid or a salt thereof chelating agent as stabilizer.

DETAILED DESCRIPTION OF THE INVENTION

Figure 1:
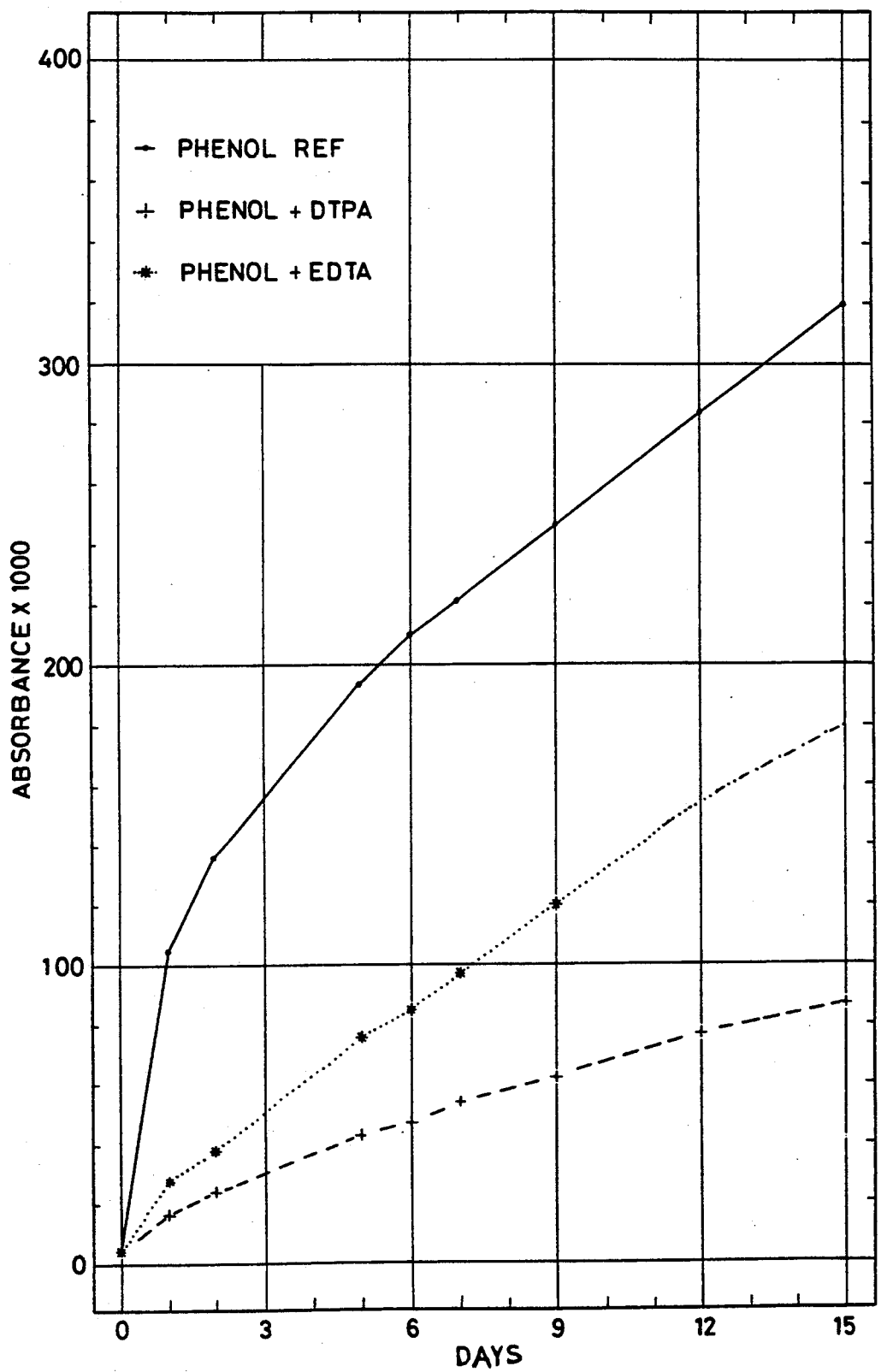

The present invention provides a chelating agent added to the conventional components of a Trinder reagent used to detect hydrogen peroxide generated in solution. Those conventional components are
a) a phenylpyrazone derivative,
b) a phenol or an aromatic amine,
c) a peroxide enzyme and
d) aqueous buffer.

Additional components may include an antimicrobial additive (e.g., sodium azide).

Exemplary phenylpyrazone derivatives include 4-aminoantipyrine and those derivatives listed at col. 9, lines 51-65 of U.S. Pat. No. 29,498 (incorporated herein by reference).

Exemplary phenols include phenol itself, 3,5-dichloro-2-hydroxybenzenesulfonic acid and various other simple and complex phenols such as those described or listed in Table I, II and III and at col. 9, lines 35 of U.S. Pat. No. 29,498 (incorporated herein by reference). Suitable compounds having aromatic amine structures include:
1) N,N-dialkylaniline compounds,
2) N,N-dialkyl-m-toluidine compounds
3) toluidine and aniline sulphopropyl derivatives,
4) N-ethyl-N-(3-sulphopropyl)-m-anisidine and
5) N-ethyl-N-(2-hydroxyethyl)-m-toluidine.

The peroxidase enzyme (POD) can be derived from a variety of microbial sources.

The aqueous buffer can be phosphate buffer establishing a neutral pH at which POD activity is high (e.g. pH 7.3) or any of various organic buffers establishing a similar pH. Additives such as antimicrobials can also be used, particularly with phosphate buffer.

A chelating agent is a compound containing donor atoms which can bond via coordination bonds to a single metal ion to form a cyclic structure known as a chelate complex or more simply a chelate (see for example Malatesta, "Chimica generale", 1980, 458).

The descriptive term "chelate" derives in fact from the word "chela"(claw of a crustacean) and symbolizes the ring which forms between the chelating agent and the metal ion.

The importance of the chelation phenomenon derives from the almost universal presence of metal ions of one species rather than another.

Chelating agents therefore provide a means for checking the presence of metal ions by the formation of complexes which generally have properties which are markedly different from those of either the ions or the chelating agents themselves.

It is this property which makes them so useful in applications in various fields.

For example their ability to sequester metal ions is used for controlling the hardness of water in industrial water treatment, for recovering minerals from crude metals, for eliminating radioactive contaminants, for various syntheses, for metal passage from one phase to another in extraction and precipitation processes, etc.

Although chelating agents are substances commonly used in various fields, including the chemical laboratory, it has only now been discovered that the use of such substances particularly in concentrations of between 0.005 mM and 50 mM and preferably between 1 mM and 10 mM results in a Trinder reagent which does not develop the aforesaid undesired spontaneous aspecific coloration.

By way of example, a description is given hereinafter of certain tested formulations which have given results enabling this important property of chelating agents of stabilizing Trinder reagents to be recognized.

With regard to the chelating agents used, particularly significant results were obtained using ethylenediaminetetraacetic acid (EDTA) and diethylenetriaminepentaacetic acid (DTPA) or their salts.

EDTA and DTPA are representative of the preferred class of chelating agents used as stabilizers: polyalkylaminepolyacetic acids and their salts. Other members of this preferred class have multiple amines linked by one or more alkylene moieties terminated by multiple acetic acid moieties which may be present in free acid or salt forms other known classes of chelating agents may also be useful, based upon corresponding effects on ions in the solution.

Color development was evaluated by measuring the absorbance of the solutions during accelerated stability at 37 deg C and 45 deg C and at ambient temperature both in the dark and in the light.

The test was carried out with two different Trinder systems with regard to the compound of phenolic or aromatic amine structure. In one case phenol was used; and in the other case N-ethyl-N-(2-hydroxy-3-suphopropyl)-m-toluidine (TOOS) was used.

The two formulations are as follows:

| EXAMPLE 1 | |
|---|---|
| Phosphate buffer pH 7.3 | 100.0 mM |
| Phenol | 3.0 mM |
| 4-aminophenazone | 0.5 mM |
| POD | 1300.0 U/l |
| Sodium azide (antimicrobic) | 15.4 mM |
| EXAMPLE 2 | |
| Phosphate buffer pH 7.3 | 100.0 mM |
| TOOS | 0.6 mM |
| 4-aminophenazone | 0.5 mM |
| POD | 1300.0 U/l |
| Sodium azide | 15.4 mM |

The chelating agents were tested in the two systems at the following concentrations:
-DTPA 0.005 M
-EDTA 0.005 M For each system the analysis was also carried out on a reference formulation without coloration inhibitors.

Absorbance spectrophotometric analysis was carried out at wavelengths corresponding to the maximum absorption of the reaction product, i.e.:
500 nm for formulations containing phenol
550 nm for formulations containing TOOS The graphs of the accompanying figures show the results of the stated experimental work, and will now be described.

In said graphs the horizontal axis represents time (in days) and the vertical axis the absorbance or extinction of the tested formulations.

Figure 2:
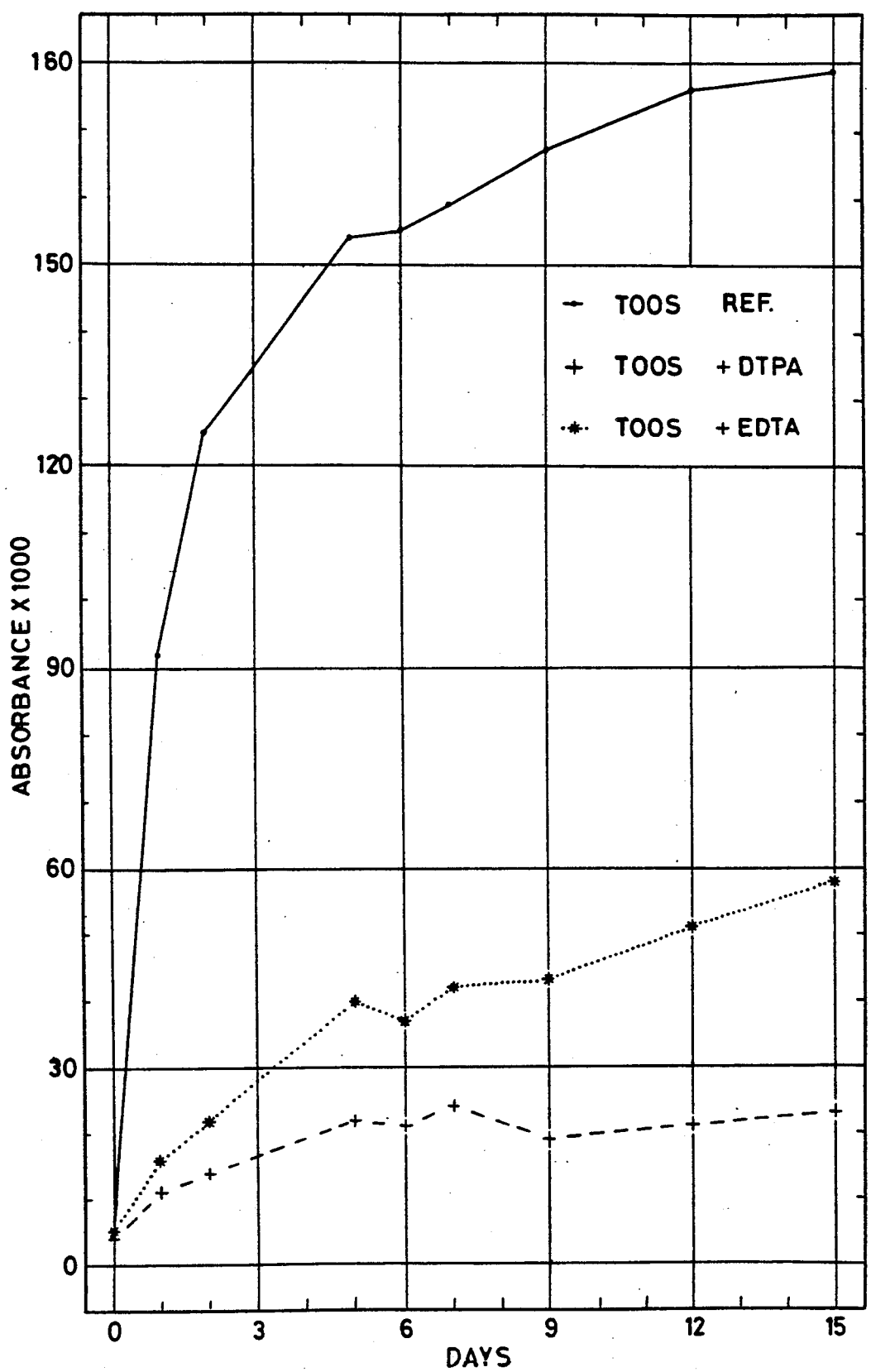

The graphs of FIGS. 1 and 2 show the color development in the systems containing phenol and TOOS, respectively, during storage at 45 deg. C. The marked reduction in coloration development in the systems containing chelating agents compared with the reference system without chelating agents is immediately apparent.

Figure 3:
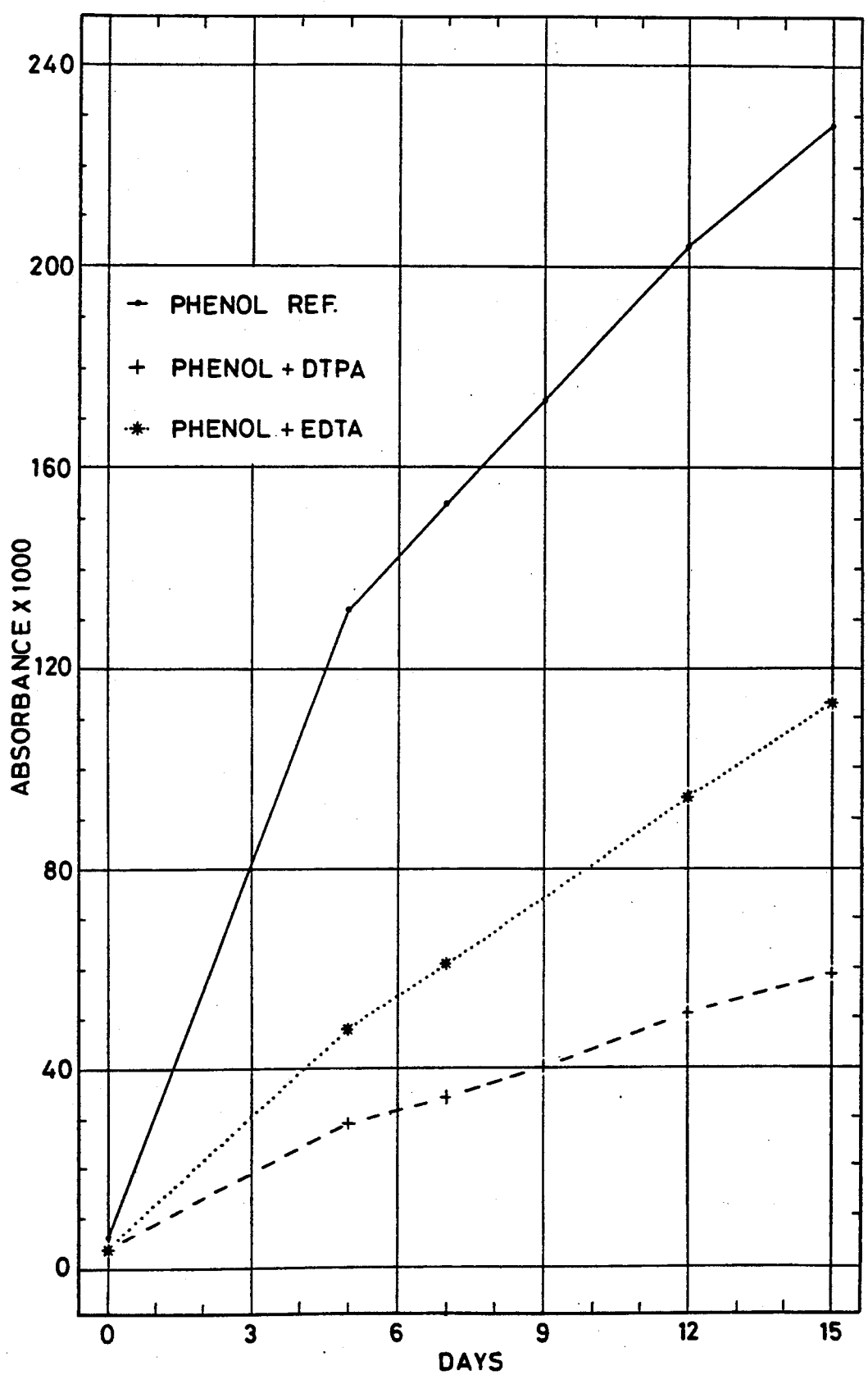
Figure 4:
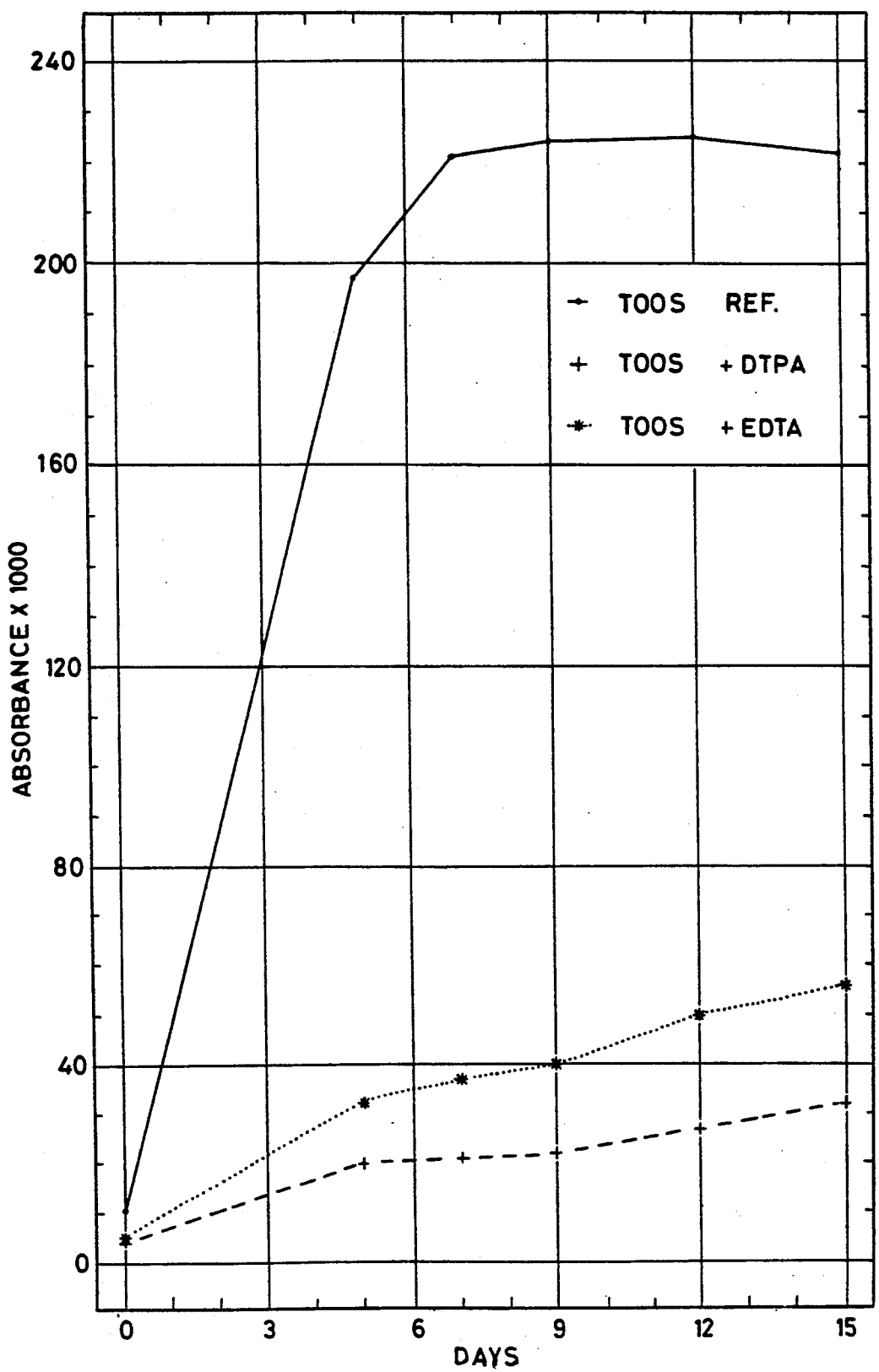

The graphs of FIGS. 3 and 4 show the color development in the systems containing phenol and TOOS, respectively, during storage at 37 deg. C. Again in this case a marked reduction in coloration development compared with the control system without chelating agents is immediately apparent.

Figure 5:
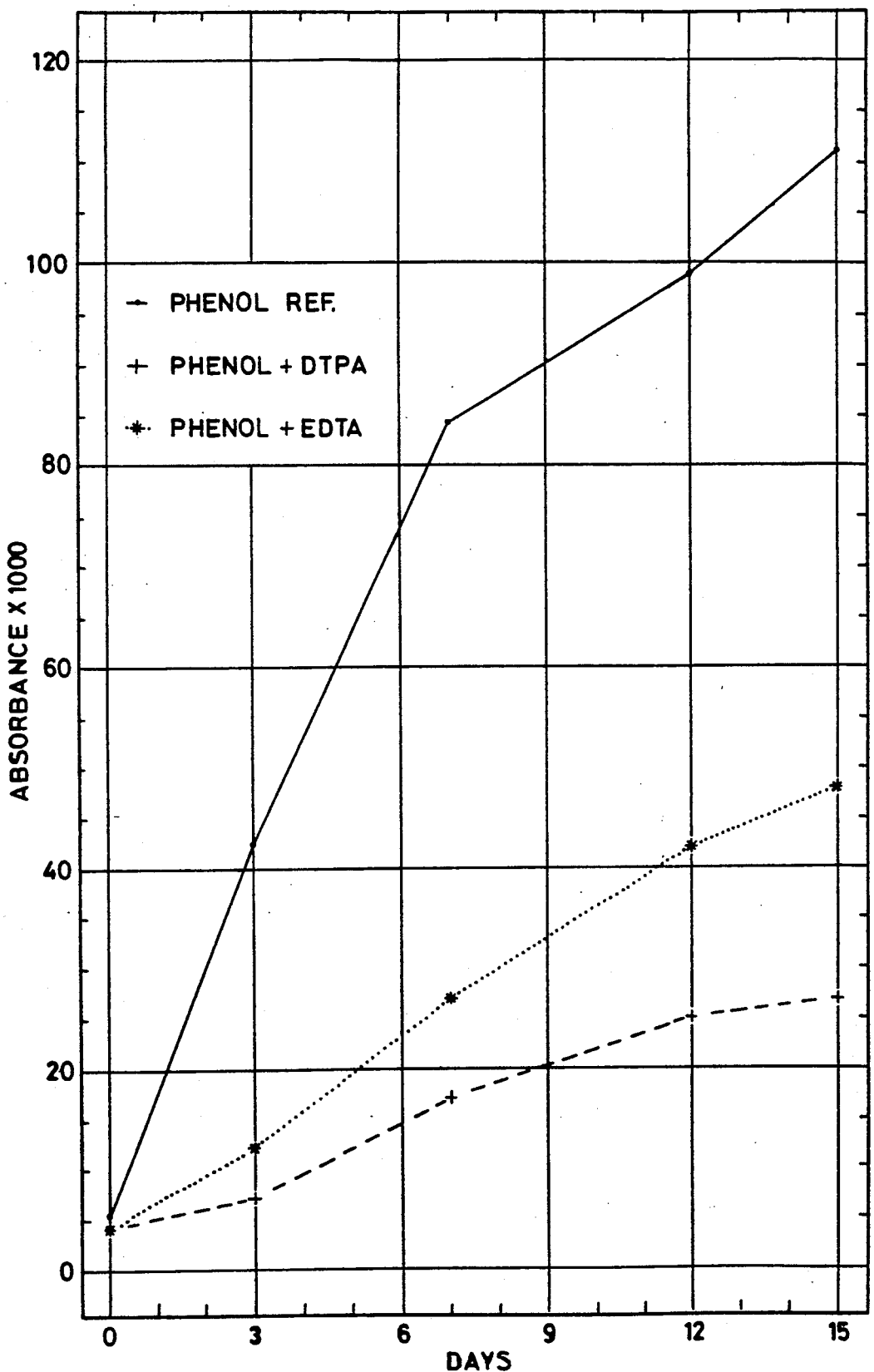
Figure 6:
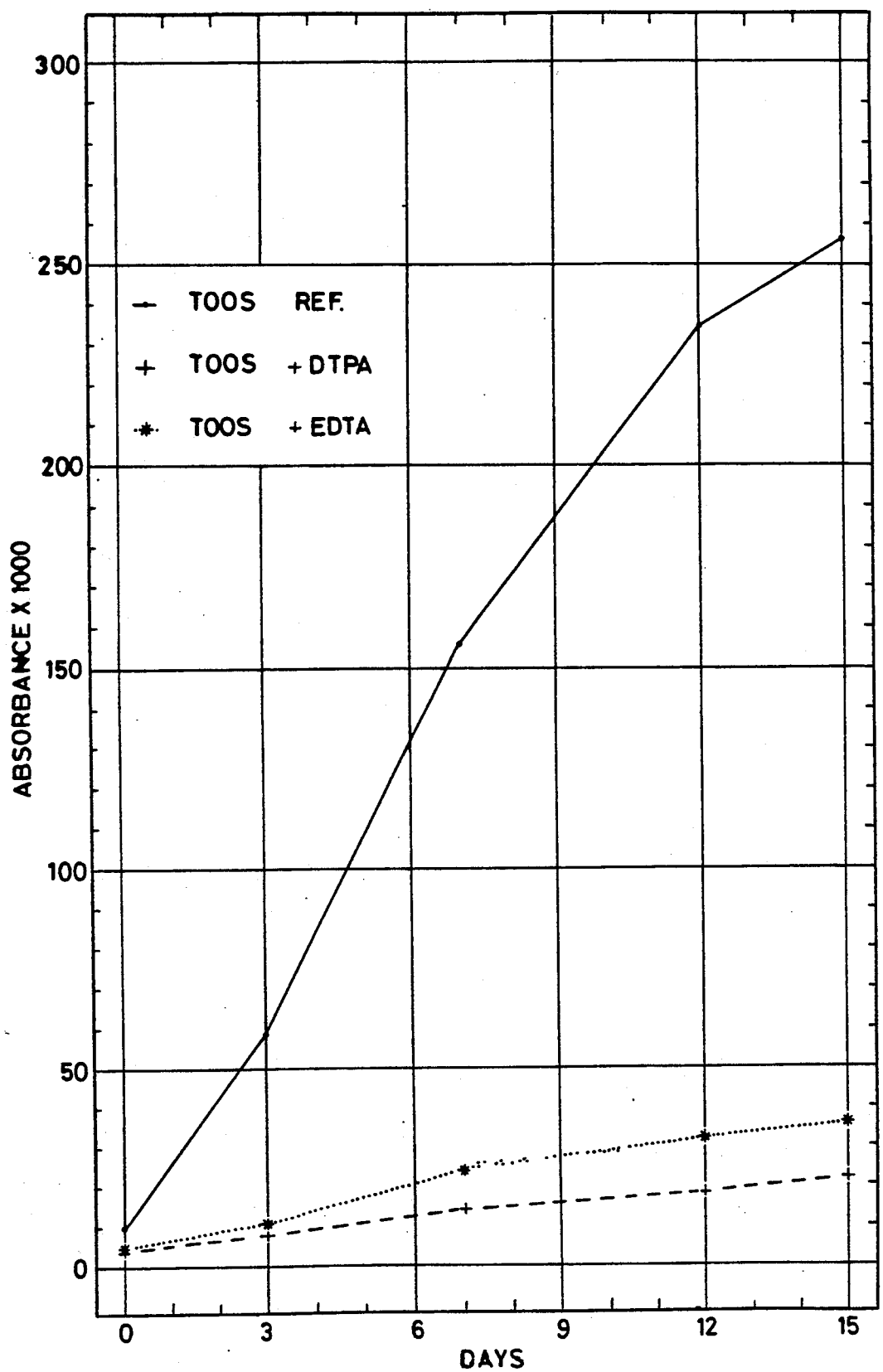

The graphs of FIGS. 5 and 6 show the color development in the systems containing phenol and TOOS, respectively, during storage at ambient temperature in the dark. The above observations for the other graphs also apply totally to FIGS. 5 and 6, the difference in behaviour between the compositions containing chelating agents and the control composition being clear.

Figure 7:
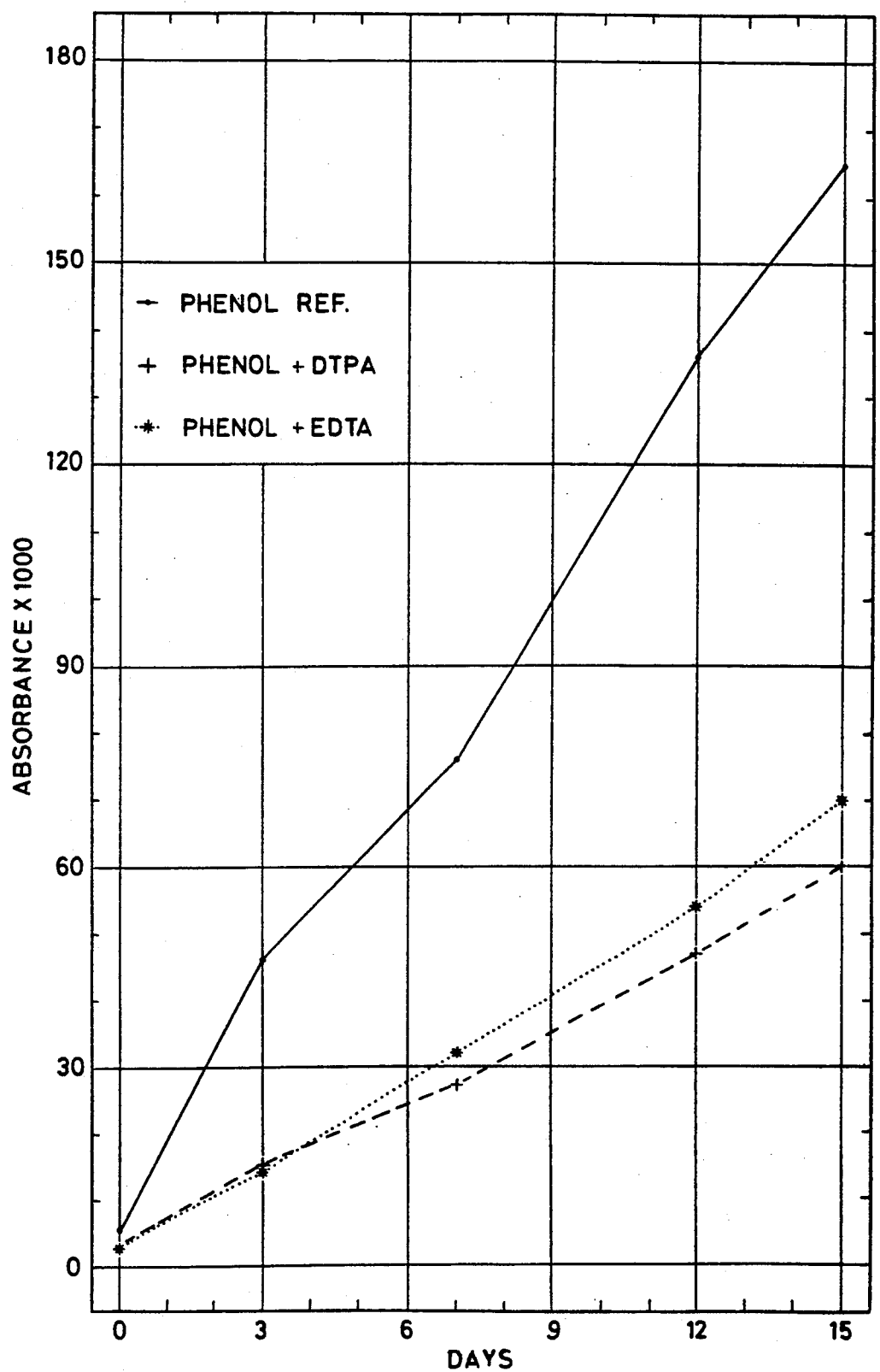
Figure 8:
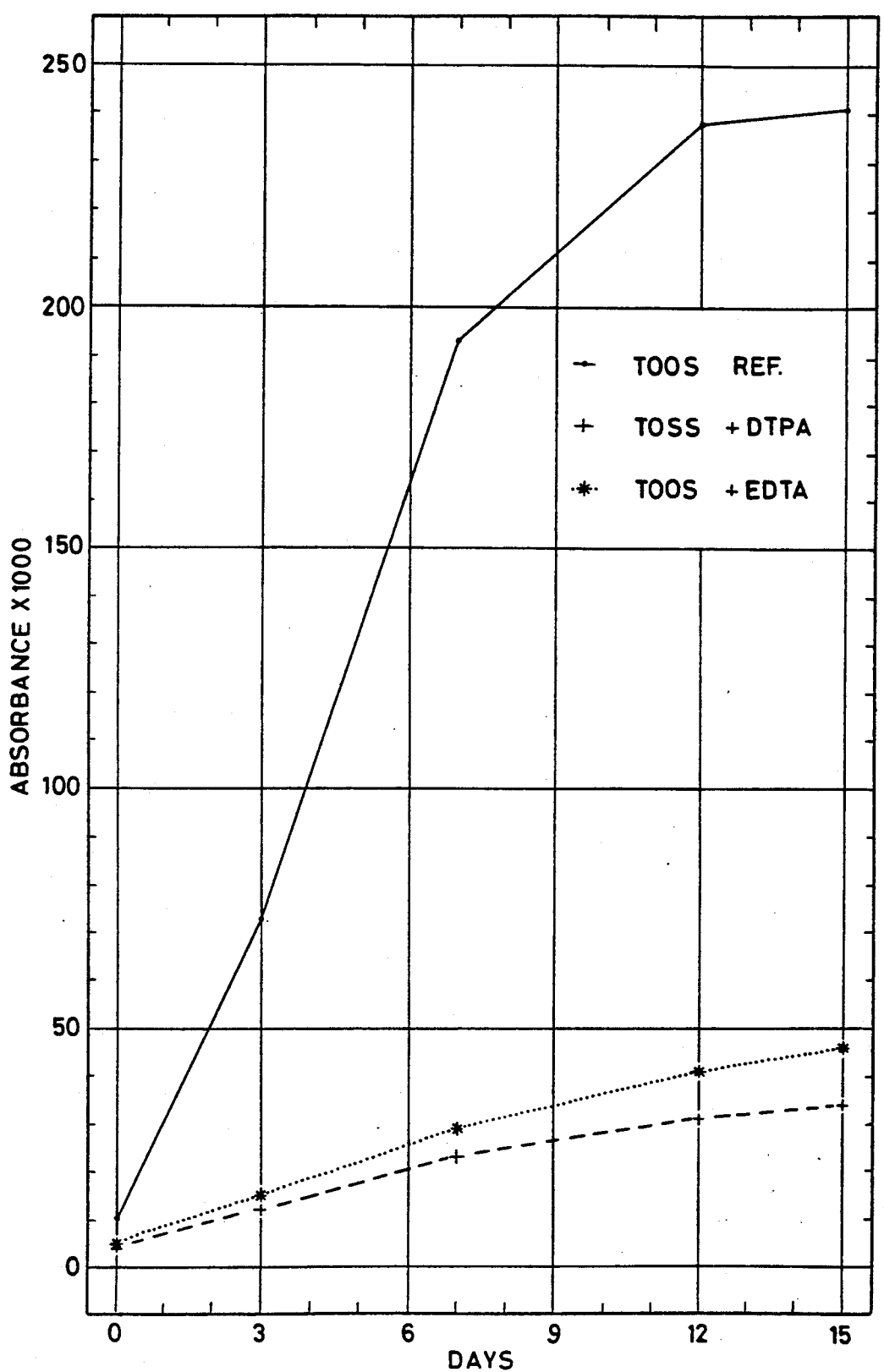

Finally, the graphs of FIGS. 7 and 8 show the color development in the systems containing phenol and TOOS, respectively, during storage at ambient temperature while exposed to light. In this case the samples were stored in transparent glass vials and illuminated by two 30 watt neon lamps each positioned 70 cm from the surface on which the vials rested. The marked reduction in coloration development due to the addition of chelating agents is again in this case very clear from the graph.

The stabilized Trinder reagent of the present invention can be used to detect hydrogen peroxide in the usual fashion. For example, a sample can be admixed with a conventional glucose oxidase reagent (or the stablized GOD reagent of Italian patent application 21591 A/89 and its counterpart filed herewith) to generate hydrogen peroxide in an amount functionally related to the glucose content of the sample. The present Trinder reagent can then be added, but is preferably present in the original reaction mixture, so as to produce chromophore in an amount stoichiometrically related to the hydrogen peroxide so generated. Such chromophore can then be detected by light absorbence. These various mixing, reacting and detecting steps can be performed utilizing multicuvette rotors and associated apparatus such as is described in U.S. Pat. No. 4,738,825.

For example, the following aqueous reagent was prepared

| Buffer (e.g. phosphate) | 100 mM | pH 7.0 |
|---|---|---|
| Phenol | 3 mM | |
| 4-AA | 0.4 mM | |
| Glucose oxidase | >5000 U/l | |
| Peroxidase | >1000 U/l | |
| DTPA | 2 mM | |

Various other elements could be added like antimicrobics, stabilizers, excipients and so on.

While the glucose oxidase and Trinder reagent are combined in this particular formulation, it is contemplated that a GOD reagent according to Italian 21591 A/89 and a Trinder reagent according to the present invention would be prepared separately, stored separately and either combined into a single reagent container when loading onto an instrument or separately aliquoted into a cuvette.

Into a reaction cuvette of a rotor (according to U.S. Pat. No. 4,738,825) were aliquoted 2.5 ml of the above combined reagent (with or without DTPA) and 0.3 ml of any of five standards, or two samples. The reaction was performed with incubation at 37 deg C and spectrophotometric analysis at 520 mm (comparing the increase in absorbance over a fixed interval to calibrated values). The results were as follows:

| | Reagent without cheating agent | Reagent with chelating agent (DTPA 2 mM) |
|---|---|---|
| Std. 50 mg/dl | 50 | 50 |
| Std. 100 mg/dl | 101 | 101 |
| Std. 200 mg/dl | 200 | 198 |
| Std. 400 mg/dl | 409 | 405 |
| Std. 600 mg/dl | 595 | 590 |
| Normal serum | 111 | 110 |
| Pathological serum | 257 | 256 |

These results show that the DTPA chelating agent did not interfere with the enzymatic reactions by which the reagent is used to measure glucose.

I claim:

1. A composition of the Trinder type for detecting hydrogen peroxide evolved in a solution, consisting essentially of:
   a) a phenylpyrazone derivative,
   b) a phenol or an aromatic amine,
   c) a peroxidase enzyme,
   d) aqueous buffer, and
   e) a chelating agent comprising a polyalkylaminepolyacetic acid or a salt thereof.

2. The composition of claim 1 wherein the polyalkylaminepolyacetic acid or salt is EDTA or a salt thereof.

3. The composition of claim 1 wherein the polyalkylaminepolyacetic acid or a salt thereof is DTFA or a salt thereof.

4. The composition of claim 1 wherein the polyalkylaminepolyacetic acid or salt thereof is present at a concentration of from about 0.005 mM to about 50 mM.

5. The composition of claim 1 wherein said concentration is in the range of from about 1 mM to about 10 mM.

6. The composition of claim 1 wherein the phenylpyrazone derivative is aminophenazone.

7. The composition of claim 1 wherein the phenylpyrazone derivative is aminophenazone.

8. The composition of claim 1 wherein the compound (b) is N-ethyl-N-(2-hydroxy-3-sulphopropyl)-m-toluidine (TOOS).

9. The composition of claim 1 wherein the phenylpyrazone derivative is 4-aminoantipyrine.

* * * * *